(12) United States Patent
Stanglmeier et al.

(10) Patent No.: US 9,605,776 B2
(45) Date of Patent: Mar. 28, 2017

(54) STOPPER FOR SEALING THE HOUSING OF AN EXHAUST GAS SENSOR, EXHAUST GAS SENSOR, AND MANUFACTURING METHOD FOR AN EXHAUST GAS SENSOR

(71) Applicants: Frank Stanglmeier, Eberdingen-Hochdorf (DE); Jens Schneider, Leonberg (DE); Bernd Rattay, Ditzingen (DE)

(72) Inventors: Frank Stanglmeier, Eberdingen-Hochdorf (DE); Jens Schneider, Leonberg (DE); Bernd Rattay, Ditzingen (DE)

(73) Assignee: Robert Bosch GmbH, Stuttgart (DE)

( * ) Notice: Subject to any disclaimer, the term of this patent is extended or adjusted under 35 U.S.C. 154(b) by 204 days.

(21) Appl. No.: 14/377,712

(22) PCT Filed: Jan. 7, 2013

(86) PCT No.: PCT/EP2013/050141
§ 371 (c)(1),
(2) Date: Aug. 8, 2014

(87) PCT Pub. No.: WO2013/117358
PCT Pub. Date: Aug. 15, 2013

(65) Prior Publication Data
US 2015/0014944 A1    Jan. 15, 2015

(30) Foreign Application Priority Data
Feb. 9, 2012 (DE) .................. 10 2012 201 900

(51) Int. Cl.
*F16L 5/10* (2006.01)
*H02G 15/013* (2006.01)
(Continued)

(52) U.S. Cl.
CPC .............. *F16L 5/10* (2013.01); *F01N 11/007* (2013.01); *G01N 27/4078* (2013.01);
(Continued)

(58) Field of Classification Search
CPC  G01N 27/4078; H02G 15/013; F01N 11/007; F01N 2560/02; F16L 5/10;
(Continued)

(56) References Cited

U.S. PATENT DOCUMENTS

| 4,415,878 A | 11/1983 | Novak |
| 5,679,226 A | 10/1997 | Furusaki et al. |

(Continued)

FOREIGN PATENT DOCUMENTS

| DE | 40 34 072 | 4/1992 |
| DE | 94 100 70 | 10/1995 |

(Continued)

OTHER PUBLICATIONS

International Search Report for PCT/EP2013/050141, dated Mar. 1, 2013.

*Primary Examiner* — Daniel S Larkin
(74) *Attorney, Agent, or Firm* — Norton Rose Fulbright US LLP; Gerard Messina

(57) ABSTRACT

A stopper for sealing a housing of an exhaust gas sensor has: a base body which contains polytetrafluoroethylene; at least one through channel for leading through a connecting cable; and a seal situated, at least in places, between the base body of the stopper and the through channel, the seal containing at least one perfluoroalkoxy polymer or one tetrafluoroethylene perfluoroproylene or one polychlorotrifluoroethylene or one polyvinylidene fluoride.

12 Claims, 5 Drawing Sheets

(51) Int. Cl.
*F01N 11/00* (2006.01)
*G01N 27/407* (2006.01)
*H01R 13/52* (2006.01)

(52) U.S. Cl.
CPC ....... *H01R 13/5208* (2013.01); *H02G 15/013* (2013.01); *Y10T 29/49826* (2015.01)

(58) Field of Classification Search
CPC .......... H01R 13/5208; Y10T 29/49826; B29C 65/02; B29C 65/48; B29K 2027/12; B29K 2027/16; B29K 2027/18
USPC ....................................................... 73/23.31
See application file for complete search history.

(56) References Cited

U.S. PATENT DOCUMENTS

| | | | | |
|---|---|---|---|---|
| 5,949,023 A | * | 9/1999 | Weyl | G01N 27/4062 174/652 |
| 6,018,982 A | * | 2/2000 | Friese | G01N 27/407 204/410 |
| 6,672,132 B1 | * | 1/2004 | Weyl | G01N 27/407 73/23.31 |
| 2007/0033986 A1 | * | 2/2007 | Wild | G01N 37/00 73/31.05 |
| 2009/0065358 A1 | | 3/2009 | Matasumoto | |

FOREIGN PATENT DOCUMENTS

| | | |
|---|---|---|
| DE | 196 31 501 | 2/1998 |
| DE | 197 28 370 | 1/1999 |
| DE | 10 2005 020793 | 11/2006 |
| DE | 10 2008 044 159 | 6/2010 |
| JP | 04285849 A | 10/1992 |
| JP | 11190717 A | 7/1999 |
| JP | 2001 103645 | 4/2001 |
| JP | 2001 242128 | 9/2001 |

* cited by examiner

STOPPER FOR SEALING THE HOUSING OF AN EXHAUST GAS SENSOR, EXHAUST GAS SENSOR, AND MANUFACTURING METHOD FOR AN EXHAUST GAS SENSOR

BACKGROUND OF THE INVENTION

1. Field of the Invention

The present invention relates to an exhaust gas sensor having: a housing in which a sensor element which, for example, is ceramic and operates electrochemically is situated; and a stopper which seals off the housing, and through which at least one connecting cable is led out of the housing or into the housing.

2. Description of the Related Art

On the one hand, this stopper and the cooperation of the stopper with the connecting cable must meet the requirement for a high level of seal-tightness. Due to the high level of seal-tightness, the penetration of harmful, for example corrosion-inducing, liquids and gases into the interior of the exhaust gas sensor may be effectively and permanently prevented. To achieve the seal-tightness it is necessary in particular for the stopper to have sufficient elasticity. On the other hand, as a result of the high exhaust gas temperatures to which the exhaust gas sensor is exposed, only materials having an appropriately high heat resistance are suitable for the stopper.

It is already known from published German patent application document DE 10 2005 020 793 A1 to provide a stopper made of polytetrafluoroethylene, also known as PTFE, for closing off the housing of an exhaust gas sensor. It is also provided to weld insulating jackets of connecting cables in through channels of this stopper, with the aid of fluoride-containing plastic.

BRIEF SUMMARY OF THE INVENTION

According to the present invention, the stopper has a base body which contains polytetrafluoroethylene (PTFE). Although the term "base body" within the context of the present invention is not to be construed as overly limiting, it is preferred that the base body of the stopper has the design or basic design of a straight circular cylinder, or is similar to same or starts from same. For example, starting from the shape or the basic shape, bevels, soundings, and/or the like may be made, and/or deformations, for example of a plastic and/or elastic nature, may be made.

"Polytetrafluoroethylene (PTFE)" is understood in particular to mean the chemical substance having the structural formula [—CF2-CF2-]n.

Since the base body of the stopper contains polytetrafluoroethylene (PTFE) according to the present invention, i.e., a material having excellent heat resistance, it is advantageous when the base body predominantly contributes to the mass and/or to the volume of the stopper. In particular, it may be advantageous for the base body to constitute at least 80% or at least 85%, preferably even at least 90% or at least 95%, of the mass of the stopper. Additionally or alternatively, it may also be advantageous for the base body to constitute at least 65% or at least 72%, preferably even at least 79% or at least 86%, of the volume of the stopper.

Although the base body may contain only a certain proportion of polytetrafluoroethylene (PTFE) in terms of its spatial portion and/or its chemical composition, it is preferred that the base body is composed of at least 95% or completely of polytetrafluoroethylene (PTFE), and/or that the base body is composed of polytetrafluoroethylene (PTFE).

According to the present invention, the stopper has at least one through channel, in particular one axial through channel, for leading through at least one connecting cable. Based, for example, on a cylindrical or cylinder-like design or basic design of the base body, an axial through channel is understood to mean that the through channel passes through the two oppositely situated end faces of the stopper, and/or that the through channel does not pass through the lateral surface of the stopper, which in particular is radially outwardly situated. Although the present invention is not limited thereto, it is preferred that the through channel extends in parallel to an axis of symmetry of the base body, or that an axis of symmetry of the base body even coincides with an axis of symmetry of the through channel. In addition, providing multiple, in particular two, three, four, five, or six, through channels is possible, these through channels preferably being situated symmetrically around an axis of symmetry of the base body. Although providing exactly one connecting cable per through channel is preferred, in principle it is also possible to provide multiple connecting cables in one through channel, or to provide a combination of connecting cables which is glued and/or welded, for example, and which includes multiple connecting cables.

According to the present invention, the stopper includes a seal which is situated, at least in places, between the base body of the stopper and the through channel. This seal is preferably suitable for closing, in particular sealing off, a gap that remains between the base body of the stopper and the through channel. Although it is possible and also preferred for the seal to line, in particular to predominantly or completely line, the inner contour of the stopper, i.e., the outer wall of the through channel, it is also possible and preferred for the seal to be situated between the base body and the through channel only in places; i.e., portions of the inner contour of the stopper and of the outer wall of the through channel remain open toward one another.

The present invention is based on the finding that the selection of the material of the seal is particularly important in achieving an improved sealing effect in the area of the seal. It has been found in particular that, although the base body, due to the material which it contains or is even made of, polytetrafluoroethylene (PTFE), has high heat resistance, it has elastic properties only to a limited extent, and therefore is less suitable for transmitting a force or a state of stress. A sealing effect based on a force fit is therefore difficult to achieve, or is achievable only incompletely. Based on this finding, it has also been recognized that the search for suitable materials for the seal should be focused on materials which are suitable for connecting to polytetrafluoroethylene (PTFE) in an integrally joined manner, i.e., suited in particular for wetting the substance polytetrafluoroethylene (PTFE).

According to the present invention, and based on the above-mentioned findings, tests by the applicant have identified the substances perfluoroalkoxy (PFA) polymer and tetrafluoroethylene perfluoropropylene (FEP) as suitable. The substances polychlorotrifluoroethylene (PCTFE) and polyvinylidene fluoride (PVDF) have likewise been identified as suitable. However, the substances polychlorotrifluoroethylene (PCTFE) and polyvinylidene fluoride (PVDF), due to their slightly lower heat resistance compared to perfluoroalkoxy (PFA) polymer and tetrafluoroethylene perfluoroproylene (FEP), are to be provided in particular only for use at lower working temperatures (for working temperatures below 210° C., for example). The use of perfluoroalkoxy (PFA) polymer and/or tetrafluoroethylene perfluoroproylene (FEP) is the preferred approach, in particular for high working temperatures (for working temperatures of up to 280° C. or even up to 305° C., for example).

Although it is preferred that the seal is made of perfluoroalkoxy polymer (PFA) or tetrafluoroethylene perfluoroproylene (FEP) or polychlorotrifluoroethylene (PCTFE) or polyvinylidene fluoride (PVDF) or a mixture of these substances, or is composed of at least 95% or completely of perfluoroalkoxy (PFA) polymer or tetrafluoroethylene perfluoroproylene (FEP) or polychlorotrifluoroethylene (PCTFE) or polyvinylidene fluoride (PVDF) or a mixture of these substances, in principle the present invention also encompasses seals which include only a portion that is composed of these substances, or which are made of a material which contains only a portion, in particular a predominant portion, of perfluoroalkoxy (PFA) polymer and/or tetrafluoroethylene perfluoroproylene (FEP) and/or polychlorotrifluoroethylene (PCTFE) and/or polyvinylidene fluoride (PVDF).

"Tetrafluoroethylene perfluoroproylene (FEP)" is understood in particular to mean the chemical substance having the structural formula [—CF2-CF2-CF(CF3)-CF2-]n. "Tetrafluoroethylene perfluoroproylene (FEP)" is understood in particular to mean chemical substances which are producible by polymerization of mixtures of the monomer tetrafluoroethylene (TFE) with a proportion of the monomer hexafluoropropylene (HFP) which is different from zero, in particular significantly different from zero.

"Perfluoroalkoxy (PFA) polymers" are understood in particular to mean chemical substances which are producible by polymerization of mixtures of the monomer tetrafluoroethylene (TFE) with a proportion of the monomer perfluoropropyl vinyl ether (PPVE) which is different from zero, in particular significantly different from zero. "Perfluoroalkoxy (PFA) polymers" are understood in particular to mean chemical substances having the structural formula [—CF2-CF2-CF(OR)—CF2-]n, where the side group OR is at least one alkoxy group. In particular, these involve fully fluorinated polymers having at least one alkoxy side chain. Perfluoroalkoxy (PFA) polymers are in particular chemical substances which are thermoplastically processable, which are able to wet ceramic, oxidic, glass, and/or metal surfaces, and/or which are fusible with polytetrafluoroethylene (PTFE). The present invention in particular encompasses various PFA qualities and/or mixtures of different PFA qualities, so-called PFA polyblends. In conjunction with the present invention, the applicant has had a particularly positive experience with PFA polyblends, whose melting range is 260° C. to 320° C., in particular 260° C. to 320° C. Polymers having a molar mass of $3*10^5$ g/mol to $3*10^6$ g/mol are preferred.

"Polychlorotrifluoroethylene (PCTFE)" is understood in particular to mean the chemical substance having the structural formula [—CFCl—CF2-]n.

"Polyvinylidene fluoride (PVDF)" is understood in particular to mean the chemical substance having the structural formula [—CH2-CF2-] n.

Although the temperature stability of the materials provided for the seal, in particular perfluoroalkoxy (PFA) polymer and tetrafluoroethylene perfluoroproylene (FEP) and polychlorotrifluoroethylene (PCTFE) and polyvinylidene fluoride (PVDF), is relatively high, it is still considerably less than the temperature stability of the material polytetrafluoroethylene (PFTE) provided for the base body. For this reason, it may be advantageous for the seal and/or the material of which the seal is made to contribute to the mass and/or to the volume of the stopper only to a small extent. In particular, it may be advantageous for the seal and/or the material of which the seal is made to constitute 20% maximum or 15% maximum, preferably even 10% maximum or 5% maximum, of the mass of the stopper. Additionally or alternatively, it may be advantageous for the seal and/or the material of which the seal is made to constitute 20% maximum or 15% maximum, preferably even 10% maximum or 5% maximum, of the volume of the stopper. In addition, seals whose volume constitutes less than 35% or less than 25%, preferably less than 15%, of the volume of the associated through channel are preferred. The overall temperature stability of the stopper is optimized by use of the mentioned measures.

In particular, it is possible for the seal to be situated on the base body in the form of a layer facing the through channel, in particular layer thicknesses of at least 10 μm, preferably at least 50 μm, having proven to be satisfactory, since an operationally reliable formation of the sealing layer is thus ensured. In this regard, a layer thickness of 1 mm, preferably 250 μm, should not be exceeded. In particularly temperature-critical applications, a layer thickness between 50 μm and 150 μm may be preferred, in particular when a fluctuation of the actual layer thickness of 20%, preferably of 15%, is not exceeded.

It is possible in principle and encompassed by the present invention for an integrally joined connection between the seal and the base body to not yet be established or not yet be completely established at the factory, and being formable or completely formable in particular during operation of the sensor, for example due to self-heating of the sensor and/or as a result of the exhaust gas sensor being acted on by hot exhaust gas. However, in one advantageous specific embodiment of the present invention, establishing this integral bond is already integrated into the manufacturing process, so that a stopper and an exhaust gas sensor are then present in which the base body is completely or partially integrally joined to the seal, and in which an optimized sealing effect is already present at the beginning of the intended operation of the sensor.

An integrally joined connection is a connection in which the joining partners are held together by the forces which become active at the molecular level, in particular as also defined in VDI Guideline 2232-2004-01. Examples of integrally joined connections are welding, adhesive bonding, fusion, etc. The integrally joined connection may in particular be a direct integrally joined connection between two joining partners, in which a direct interaction between the two joining partners results at the molecular level. On the other hand, the integrally joined connection may in particular also be an indirect integrally joined connection in which the two joining partners are not directly connected to one another in an integrally joined manner, but instead are each directly integrally connected to at least one third joining partner, and in the case of multiple third joining partners, all of these third joining partners are (indirectly or directly) connected to one another in an integrally joined manner.

One refinement of the present invention is a stopper for sealing a housing of an exhaust gas sensor, the stopper including a base body which contains polytetrafluoroethylene, the stopper having at least one through channel, in particular one axial through channel, through which an electrical conductor is led, an insulating seal being situated, at least in places, between the base body of the stopper and the through channel, and together with the electrical conductor being led out of the stopper at least on one side, i.e., in particular on at least one end-face side of the stopper, the insulating seal containing at least one perfluoroalkoxy polymer or one tetrafluoroethylene perfluoroproylene or one polychlorotrifluoroethylene or one polyvinylidene fluoride. The insulating seal in particular faces the electrical conductor and the base body directly, and is connected or connectable in particular in an integrally joined manner, in particular weldable, to the electrical conductor and/or to the base body, in particular within the through channel. Refinements of this subject matter having one or more of the features provided in the claims and/or the description of the present invention, in particular in conjunction with the other exemplary embodiments, are possible. In particular, it is also always possible to design the seal of the stopper and the insulation of the connecting cable as a single part.

The stopper according to the present invention has a through channel, in particular an axial through channel, for leading through a connecting cable. This means that the through channel is basically provided in such a way that a connecting cable may be led through the stopper, and preferably may be led through the stopper from the interior of the housing into an area outside the housing.

One refinement of the present invention provides that the stopper includes a connecting cable which is led through the stopper, preferably led through the stopper from the interior of the housing into an area outside the housing.

In the present context, an exhaust gas sensor is understood in particular to mean a lambda sensor for use in the exhaust tract of an internal combustion engine, although it may also involve other sensors, such as a temperature sensor, a NOx sensor, a soot particle sensor, or the like. In particular, all sensors which are suitable for long-term use at high temperatures and/or in an aggressive environment, and sensors in which an electrical connecting line, for example, is to be led out of a housing to be sealed, in particular at comparatively high ambient temperatures, are encompassed by the present invention.

It is preferred that, due to providing the measures according to the present invention, seal-tightness of the housing of the exhaust gas sensor on the connection side results which is comparatively high, for example, a helium seal-tightness of less than 10^−3 mbar*L/s or 10^−4 mbar*L/s, preferably even a helium seal-tightness of less than 10^−5 mbar*L/s or 10^−6 mbar*L/s. On the other hand, the terms "seal," "sealed off," etc. should not be interpreted too narrowly, so that in particular even a purely macroscopic closure may be encompassed. In addition, a possibly remaining leak through the interior of tube-shaped insulation of the connecting cable or of the connecting cables is not taken into consideration, since this leak may be sealed off at another location, for example, at a plug which is connected to the connecting cable and the connecting cables. In addition, it may be provided to lead out such a leak through the connecting cable or the connecting cables into a noncritical area, such as a colder, less exposed area of a motor vehicle. Although an absolute or hermetic seal-tightness (in particular a helium seal-tightness of less than 10^−10 mbar*L/s) is possible in principle, it is virtually cost-prohibitive with the exception of specific applications.

To achieve comparatively high seal-tightness of the housing, it is particularly preferred for the connecting cable to be connected to the seal in an integrally joined manner. In particular, the connecting cable includes an electrical conductor which is enclosed by insulation, and the integral bond between the seal and the connecting cable is formed between the seal and the insulation of the connecting cable. The insulation of the connecting cable may in particular contain a fluoropolymer, for example polytetrafluoroethylene (PTFE), or may be made of polytetrafluoroethylene (PTFE), and in particular may be completely, predominantly, or partially made of polytetrafluoroethylene (PTFE). For optimizing the seal-tightness and the heat resistance, it is even preferred for the insulation of the connecting cable to be made of the same material as the base body of the stopper, for example polytetrafluoroethylene (PTFE).

The electrical conductor of the connecting cable is advantageously provided by Cu and/or Cu-steel litz wires.

Preferred refinements of the present invention result from the fact that the basic concept of the seal between the base body of the stopper and the connecting line is transferred to the seal between the base body of the stopper and the housing of the sensor by providing the seal according to the present invention.

Thus, as one refinement it may be provided that the stopper includes an outer seal which is situated radially outwardly on the stopper, the outer seal containing at least one perfluoroalkoxy (PFA) polymer or one tetrafluoroethylene perfluoroproylene (FEP) or one polychlorotrifluoroethylene (PCTFE) or one polyvinylidene fluoride (PVDF). In addition, the base body may be connected to the outer seal in an integrally joined manner. Additionally or alternatively, the outer seal may be situated on the base body in the form of a layer, preferably having a layer thickness of 10 μm to 1 mm, particularly preferably 50 μm to 250 μm. Additionally or alternatively, it may be provided that the housing of the exhaust gas sensor is connected to the stopper in an integrally joined manner via the outer seal.

In particular, it may be provided that the same material is provided for the outer seal and for the seal, i.e., in particular a material having the same chemical composition. In addition, the layer thicknesses provided for the seal and for the outer seal may be the same.

To achieve comparatively high seal-tightness of the housing, it is particularly preferred for the connecting cable, the stopper, and the housing to be connected to one another in an integrally joined manner, i.e., in particular an integral bond being established between the housing and the stopper, and an integral bond being established between the stopper and the connecting cable, in particular between the stopper and an insulation of the connecting cable. In particular, an overall integrally joined seal of the end of the housing of the exhaust gas sensor on the connection side is achieved.

Methods according to the present invention for manufacturing a stopper, in particular a stopper according to the present invention, and/or an exhaust gas sensor, in particular an exhaust gas sensor according to the present invention, provide a base body having at least one through channel, in particular one axial through channel, which contains polytetrafluoroethylene (PTFE), and which in particular is made of polytetrafluoroethylene (PTFE). In addition, it is provided that a connecting cable which on the radial exterior contains a sealing material containing at least one perfluoroalkoxy (PFA) polymer or one tetrafluoroethylene perfluoroproylene (FEP) or one polychlorotrifluoroethylene (PCTFE) or one polyvinylidene fluoride (PVDF) is provided. In particular, a connecting cable may be provided that includes an electrical conductor which is enclosed by an insulation which in particular contains a fluoropolymer, for example polytetrafluoroethylene (PTFE), or which is made of polytetrafluoroethylene (PTFE), for example, in addition the sealing material, which contains at least one perfluoroalkoxy (PFA) polymer or one tetrafluoroethylene perfluoroproylene (FEP) or one polychlorotrifluoroethylene (PCTFE) or one polyvinylidene fluoride (PVDF), being radially outwardly situated on this insulation. In addition, it is provided that the connecting cable is led through the axial through channel of the base body so that the sealing material enters into the through channel.

The sealing material may in particular be at least one tube, in particular a tube which is pushed onto, pulled over, or rolled onto the connecting cable. The length of the tube in the axial direction is preferably greater than its diameter. Tubes having a wall thickness of 10 µm to 1 mm are preferred, and tubes having a wall thickness of 50 µm to 250 µm are particularly preferred.

On the other hand, the sealing material may also be at least one film, in particular a film which is wound onto or around the connecting cable. Films having a wall thickness of 10 µm to 1 mm are preferred, and films having a wall thickness of 50 µm to 250 µm are particularly preferred.

On the other hand, the sealing material may also have a ring-shaped design. The sealing material may in particular be pushed onto the connecting cable, or rolled onto the connecting cable into the intended position. The length of the ring in the axial direction is preferably less than or equal to its diameter. Rings having a wall thickness of 10 µm to 1 mm are preferred, and rings having a wall thickness of 50 µm to 250 µm are particularly preferred.

In principle, the sealing material may also be introduced in some other way. For example, the sealing material in the liquid state may be injected onto the connecting cable or into the through channel.

It is provided in particular that the combination of the base body, sealing material, and connecting cable is heated at the factory. This results in particular in melting on of the sealing material, and subsequently in particular results in an integrally joined connection between the base body, sealing material, and connecting cable. Alternatively, it is possible for the heating of the combination of the base body, sealing material, and connecting cable to take place not at the factory, but instead in particular not until the initial operation of the sensor. Here as well, an integrally joined connection between the base body, sealing material, and connecting cable may result.

Heating to 285° C. to 310° C. is preferred, it being further preferred that heating to higher temperatures does not occur. In particular, heating of the stopper to higher than 327° C. does not occur.

It is provided in particular that the combination of the base body, sealing material, and connecting cable is caulked, in particular by an externally applied pressure of 700 N/cm^2 to 2000 N/cm^2. The caulking may in particular take place at the same time as the heating. In particular, the formation of an integrally joined connection between the base body, sealing material, and connecting cable may take place during the caulking.

Preferred refinements and alternatives of the manufacturing method according to the present invention result from transferring the basic concept of the seal between the base body of the stopper and the connecting line to the seal between the base body of the stopper and the housing of the sensor by providing the seal according to the present invention.

Thus, it may be provided that the above-described outer seal between the base body of the stopper and the housing of the exhaust gas sensor is produced in addition to the seal between the base body of the stopper and the connecting line. For this purpose, an outer sealing material which contains at least one perfluoroalkoxy polymer or one tetrafluoroethylene perfluoroproylene or one polychlorotrifluoroethylene or one polyvinylidene fluoride, is situated together with the base body within the housing in such a way that the outer sealing material is situated between the base body and the housing.

In particular, a combination of the housing, outer seal, base body, sealing material of the seal, and connecting cable is produced, and the entire combination is jointly heated and caulked, in particular by an externally applied pressure of 700 N/cm^2 to 2000 N/cm^2.

In addition, during this heating it may be provided that, in addition to the sealing material, the outer sealing material is at least partially melted on, in particular at the same time, and an integrally joined connection between the base body of the stopper and the outer sealing material, and between the outer sealing material and the housing of the exhaust gas sensor, is subsequently formed.

It is particularly advantageous when the sealing material to be introduced has the same chemical composition and handling characteristics as the outer sealing material to be introduced. For example, the sealing material and the outer sealing material may both be processed in the form of fusible films 100 µm to 200 µm thick.

DETAILED DESCRIPTION OF THE INVENTION

Figure 1A:
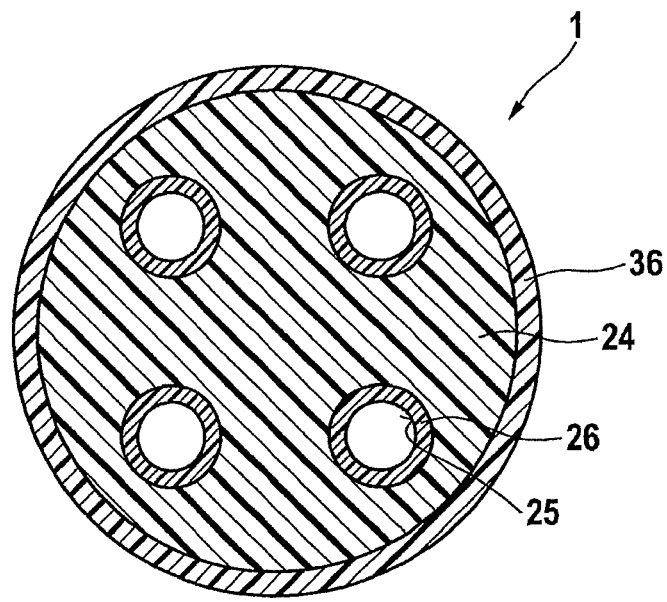
FIGS. 1a and 1b, 2a and 2b, 3a and 3b, and 4a and 4b, in each case in the top view and in a section along a longitudinal axis of the stopper, show example embodiments of the stopper according to the invention.
Figure 1B:
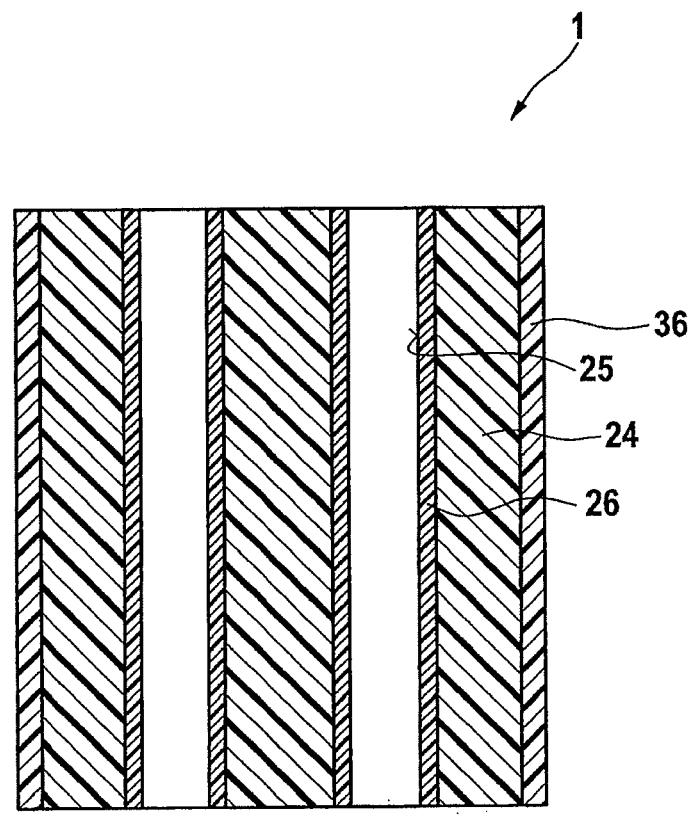

FIGS. 1a and 1b show a first exemplary embodiment of a stopper 1 according to the present invention in the top view and in a section along the longitudinal axis of stopper 1.

Stopper 1 has a cylindrical design or basic design, in particular the design or basic design of a straight circular cylinder. A radially inwardly situated base body 24 likewise has a cylindrical design or basic design, in particular the design or basic design of a straight circular cylinder. Base body 24 may have a length of 15 mm and a diameter of 10 mm, for example. Stopper 1 and base body 24 have, for example, four axial through channels 25 which extend in the longitudinal direction and have a diameter of 1 mm, for example. In this exemplary embodiment of a stopper 1 according to the present invention, through channels 25 are open, and are provided for leading through a connecting cable 21 in each case (see FIGS. 3 through 5). A seal 26 is provided in each case on the inner contours of base body 24, i.e., radially outwardly bordering through channels 25, over the entire surface in the form of a layer 100 µm thick, for example. An outer seal 36, likewise over the entire surface in the form of a layer 100 µm thick, for example, is radially outwardly applied on the lateral surface of base body 24.

In the present example, base body 24 is composed of polytetrafluoroethylene (PTFE), and constitutes over 95% of the volume or the mass of stopper 1, resulting in high thermal stability of stopper 1. In the present example, the material of seal 26 and of outer seal 36 in each case is a perfluoroalkoxy (PFA) polymer having a melting range of 260° C. to 320° C. Alternatively, the material of seal 26 and of outer seal 36 is one of the following materials: perfluoroalkoxy (PFA) polymer, tetrafluoroethylene perfluoroproylene (FEP), polychlorotrifluoroethylene (PCTFE), polyvinylidene fluoride (PVDF). Other materials which contain the mentioned materials only in part and/or mixtures of the mentioned materials are also suitable in principle.

It is provided that a housing 11 of an exhaust gas sensor 2 (see FIG. 5) is sealable by stopper 1 according to the present invention, base body 24 of stopper 1 being sealable with respect to a connecting cable 21 via seal 26, and base body 24 of stopper 1 being sealable with respect to housing 11 of exhaust gas sensor 2 via outer seal 36.

To improve the sealing effect of seal 26 and of outer seal 36, in the present example it is provided that seal 26 and base body 24 are connected to one another in an integrally joined manner by fusion, and that outer seal 36 and base body 24 are connected to one another in an integrally joined manner by fusion. In particular, it is provided that the fusion results in melting or melting-on of the material of seal 26 and of outer seal 36. In particular, it is provided that the fusion does not result in melting or melting-on or chemical decomposition of the material of base body 24.

Figure 2A:
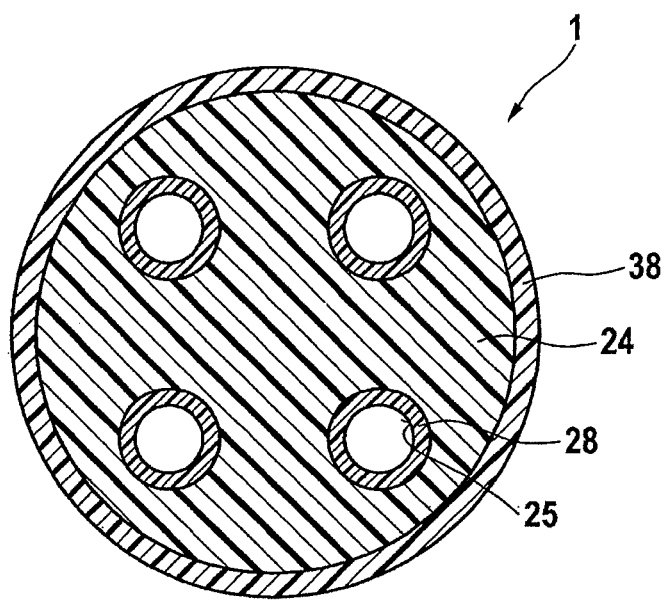
Figure 2B:
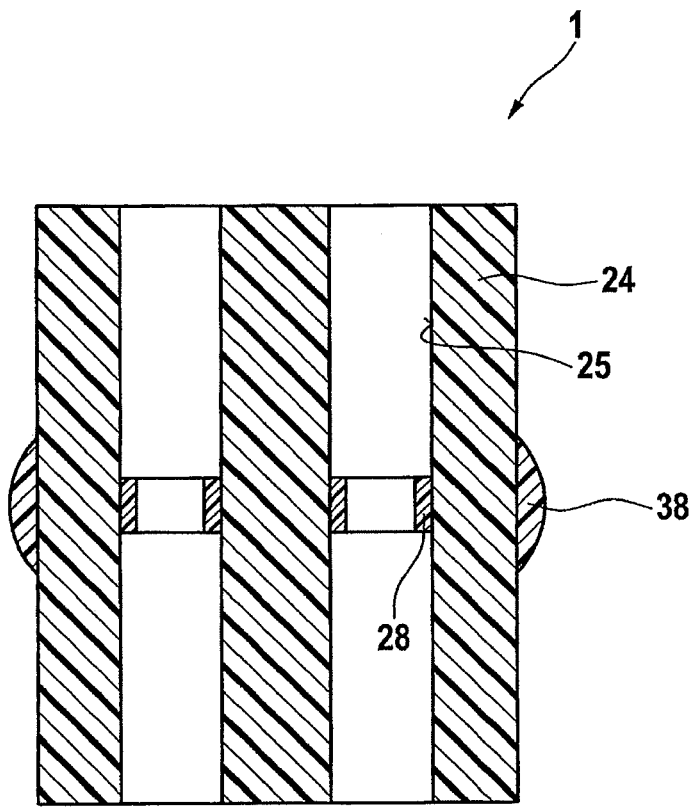

FIGS. 2a and 2b show a second exemplary embodiment of a stopper 1 according to the present invention in the top view and in a section along the longitudinal axis of stopper 1.

The second exemplary embodiment differs from the first exemplary embodiment in that seal 26 is designed not as a layer on the inner contour of base body 24 over the entire surface, but, rather, as a sealing ring 28 which is situated on the inner contour of the base body and which only partially covers same in the longitudinal extension. Sealing ring 28 has a length (in the longitudinal direction of through channel 25) of 1 mm and a thickness (in the radial direction) of 150 μm or 250 μm.

Furthermore, the second exemplary embodiment differs from the first exemplary embodiment in that outer seal 36 is designed not as a radially outer layer over the entire surface of base body 24, but, rather, as an outer sealing ring 38 which is radially outwardly situated on base body 24 and which only partially covers the outer surface of base body 24 in the longitudinal extension. Outer sealing ring 38 has a length (in the longitudinal direction of base body 24) of 3 mm and a thickness (in the radial direction) of 250 μm or 600 μm.

In the present example, sealing ring 28 and outer sealing ring 38 are situated approximately centrally, in particular centrally, in the longitudinal direction of stopper 1. In alternatives of the exemplary embodiment, it may also be provided that sealing ring 28 and/or outer sealing ring 38 is/are situated off-center. In particular, it is also possible to provide two sealing rings 28 and/or two outer sealing rings 38 which are situated opposite one another, viewed in the longitudinal direction of stopper 1. Providing even more sealing rings 28 and/or outer sealing rings 38 is also possible in principle.

Figure 3A:
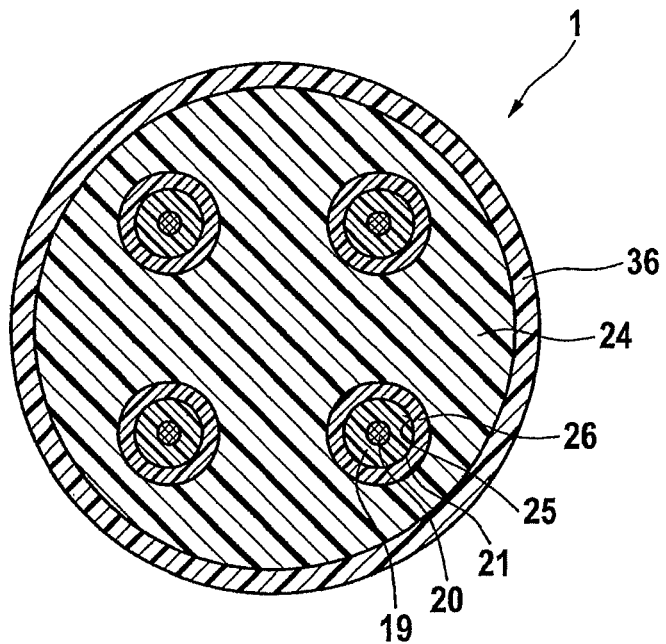
Figure 3B:
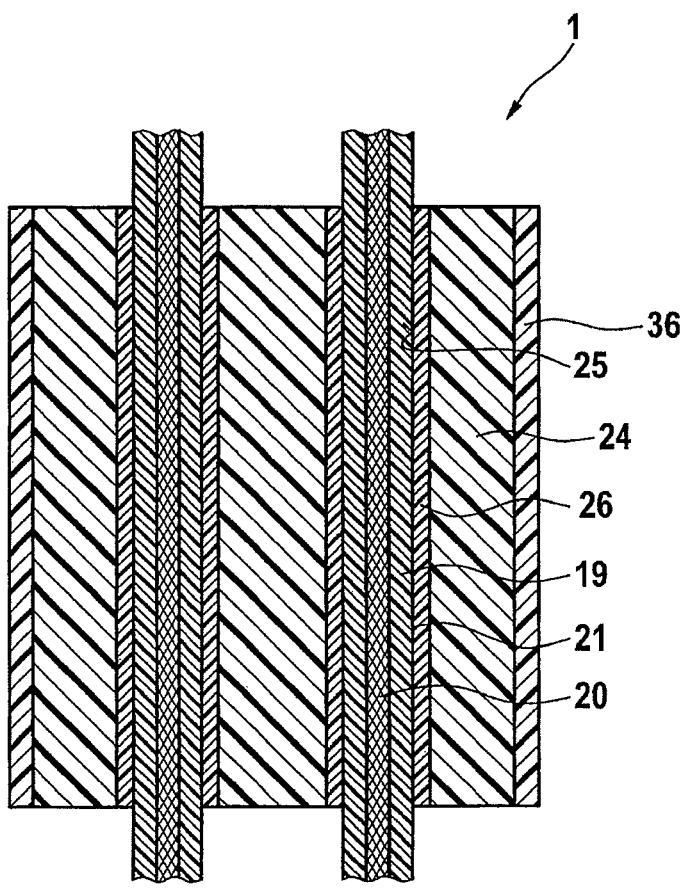

FIGS. 3a and 3b show a third exemplary embodiment of a stopper 1 according to the present invention in the top view and in a section along the longitudinal axis of stopper 1.

One refinement of the present invention, for example according to the first or second exemplary embodiment, involves a stopper 1 in which at least one connecting cable 21 is situated in through channel 25, or in which at least one connecting cable 21 is led through through channel 25 of the stopper, so that the stopper is suited in particular for sealing off housing 11 of an exhaust gas sensor 2.

In the present case, connecting cable 21 is composed of an electrical conductor 20 which in particular is made of copper litz wire or steel-copper litz wire, electrical conductor 20 in particular being enclosed by an insulation 19, in particular enclosed by an insulation 19 along the entire length of stopper 1. Alternatively, it would also be possible for electrical conductor 20 to be enclosed by an insulation 19 along only a portion of stopper 1, and along a portion of stopper 1 to directly face seal 26 and/or sealing ring 28 and/or base body 24 of stopper 1.

It may be provided that connecting cable 21, in particular insulation 19, is integrally joined, in particular fused, to seal 26 and/or to sealing ring 28, in particular by melting on the material which is provided for seal 26 or sealing ring 28.

Alternatively, however, it may also be provided that connecting cable 21, in particular insulation 19, is not integrally joined to seal 26 and/or to sealing ring 28, but, rather, is secured, in particular in a force-fit manner, solely in the interior of seal 26 and/or sealing ring 28 or in the interior of base body 24. In this case, however, it is particularly preferred that connecting cable 21, in particular insulation 19, is connectable in an integrally joined manner, in particular weldable, to seal 26 and/or to sealing ring 28.

Figure 4A:
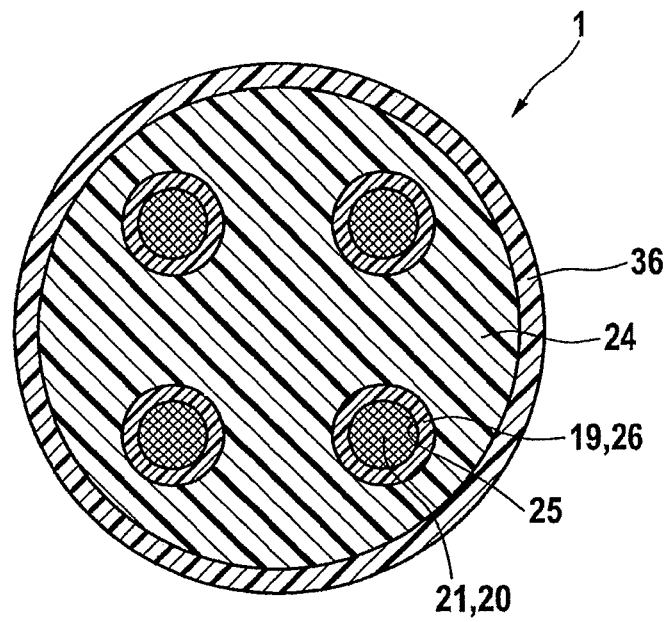
Figure 4B:
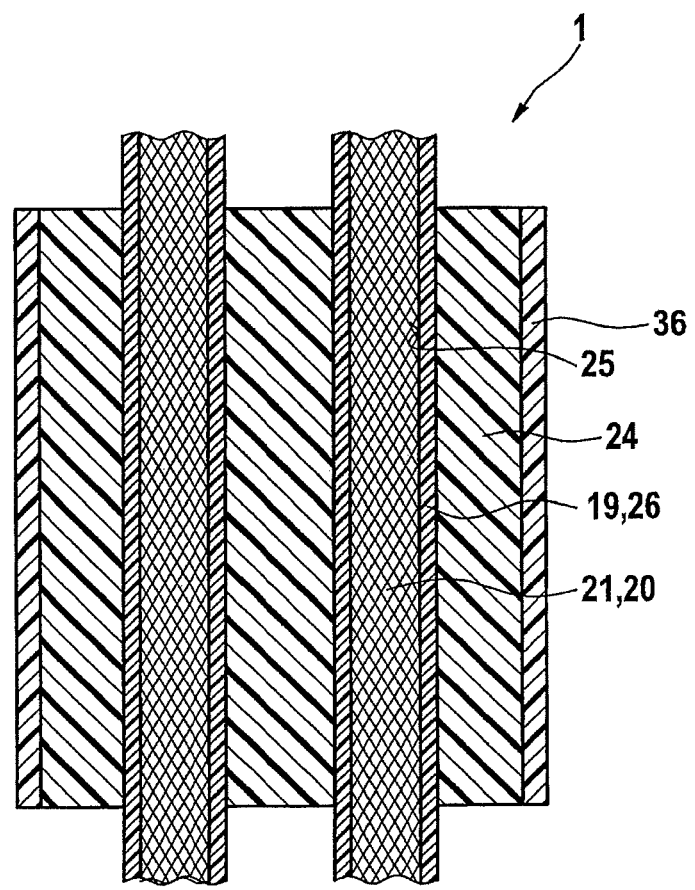

FIGS. 4a and 4b show a fourth exemplary embodiment of a stopper 1 according to the present invention in the top view and in a section along the longitudinal axis of stopper 1.

One refinement of the present invention, for example according to the first or second exemplary embodiment, involves a stopper 1 in which at least one connecting cable 21 is situated in through channel 25, or in which at least one connecting cable 21 is led through through channel 25 of the stopper, so that stopper 1 is suited in particular for sealing off housing 11 of an exhaust gas sensor 2.

In contrast to the third exemplary embodiment, it is provided that insulation 19 of connecting cable 21 and seal 26 are not designed as parts which are different from one another; instead, seal 26 at the same time takes on the function of insulation 19 of electrical conductor 20, and faces same, in particular directly. In the present example, seal 26 and insulation 19 together with electrical conductor 20 are led out of stopper 1 in particular on two sides or on one side, and insulate electrical conductor 20 of connecting cable 21 also outside of stopper 1, for example up to a portion of a plug-in connection (not shown), for example a plug, which is connected to connecting cable 21 on the side of connecting cable 21 opposite from stopper 1, and which is connectable to, in particular pluggable into, a complementary part of the plug-in connection, a socket, for example, which is part of a control unit.

In the present example, insulation 19, which at the same time forms insulation 26 within stopper 1, is designed as a 250-μm thick layer of perfluoroalkoxy (PFA) polymer which radially outwardly encloses the electrical conductor in the form of an insulation tube.

In the present example, it may be provided that insulation 19, i.e., in the present case seal 26, is integrally joined, in particular fused, to conductor 20 of connecting cable 21 and/or to base body 24 of stopper 1, in particular by melting on the material which is provided for insulation 19, i.e., in the present case seal 26.

Alternatively, however, it may also be provided that insulation 19, i.e., in the present case seal 26, is not integrally joined to conductor 20 of connecting cable 21 and/or to base body 24 of stopper 1, but, rather, insulation 19, i.e., in the present case seal 26, is secured, in particular in a force-fit manner, to conductor 20 of connecting cable 21 and/or to base body 24 of stopper 1. In this case, however, it is particularly preferred that insulation 19, i.e., in the present case seal 26, is connectable in an integrally joined manner, in particular weldable, to conductor 20 of connecting cable 21 and/or to base body 24 of stopper 1.

In alternatives of the exemplary embodiment, it may also be provided that insulation 19, which at the same time forms insulation 26 within stopper 1, is not made of a perfluoroalkoxy (PFA) polymer, but, rather, is made of a material which contains at least one perfluoroalkoxy (PFA) polymer or one tetrafluoroethylene perfluoroproylene (FEP) or one polychlorotrifluoroethylene (PCTFE) or one polyvinylidene fluoride (PVDF), in particular a material which is electrically insulating and which is heat-resistant up to or above 190° C.

The fourth exemplary embodiment is in particular also an exemplary embodiment for a stopper 1 for sealing housing 11 of an exhaust gas sensor 2, stopper 1 including a base body 24 which contains polytetrafluoroethylene, stopper 1 having at least one axial through channel 25 through which an electrical conductor 20 is led, an insulating seal 26 being situated, at least in places, between base body 24 of stopper 1 and through channel 25, the seal together with electrical conductor 20 being led out of stopper 1 at least on one side, i.e., in particular on an end-face side of stopper 1, insulating seal 26 containing at least one perfluoroalkoxy polymer or one tetrafluoroethylene perfluoroproylene or one polychlorotrifluoroethylene or one polyvinylidene fluoride. Insulating seal 26 faces, in particular directly, electrical conductor 20 and base body 24, and in particular is connected or connectable in particular in an integrally joined manner, in particular is welded or weldable, to electrical conductor 20 and/or to base body 24, in particular within through channel 25.

Further exemplary embodiments of the present invention relate to exhaust gas sensors 2 having a stopper 1, such as described above, for example, in particular in the first, second, third, and fourth exemplary embodiments (not illustrated in greater detail). These exhaust gas sensors 2 each have at least one housing 11 which is sealed off by stopper 1, and at least one connecting cable 21 which is led through through channel 25 of stopper 1.

Figure 5:
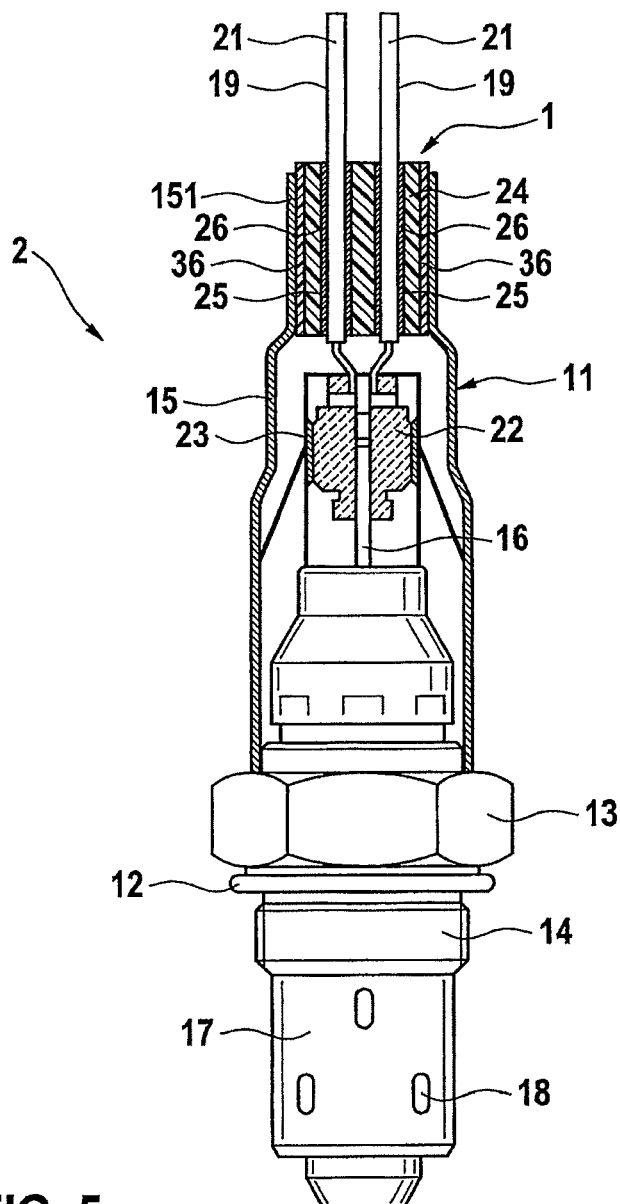
FIG. 5 shows an exhaust gas sensor according to the present invention.

As another exemplary embodiment of the present invention, an exhaust gas sensor 2 is shown in FIG. 5, whose portion on the exhaust gas side of stopper 1 is known in principle from the related art, and which is designed, for example, as part of a lambda sensor for measuring the oxygen concentration in the exhaust gas of internal combustion engines. This exhaust gas sensor 2 includes a housing 11 composed of a solid housing body 12 made of metal and having a screw thread 14, a mounting hexagon 13, and a protective sleeve 15 which is pushed onto housing body 12 and is fixedly connected thereto, and which has an end section 151 that is remote from the housing body and reduced in diameter, for example. Situated in housing 11 is a sensor element 16 which at one end on the measuring gas side protrudes from housing 11, and which at that location is covered by a protective tube 17 which has gas passage holes 18 and is fastened to housing body 12. At the end on the connection side, facing away from the end on the measuring gas side, sensor element 16 has contact surfaces which via printed conductors are connected to measuring electrodes situated at the end on the measuring gas side. Electrical conductors 20, which are enclosed by an insulation 19, for example, are contacted by connecting cables 21 on the contact surfaces. In the present exemplary embodiment, a two-part ceramic clamping body 22 which is externally enclosed by a spring element 23 and which presses electrical conductors 20 onto the contact surfaces of sensor element 16 in a force-fit manner is provided for contacting contact surfaces and electrical conductors 20. Ceramic clamping body 22 is radially supported on protective sleeve 15.

In addition, alternatives to this portion of an exhaust gas sensor 2, which is situated on the exhaust gas side of a stopper 1 and explained as an example, are possible in principle and/or likewise known from the related art.

In the further exemplary embodiments it is provided that stopper 1 closes or seals off housing 11, in that the stopper is situated in the portion of protective sleeve 15 facing away from housing body 12, in particular in an end section 151 of protective sleeve 15 remote from the housing body.

Stopper 1, as illustrated in FIG. 5, may for example be stopper 1 which is explained in conjunction with the third exemplary embodiment of the present invention (FIG. 3). Alternatively, it may be a stopper 1 as explained in conjunction with the first, second, and/or fourth exemplary embodiments (FIGS. 1, 2, and 4).

In the further exemplary embodiments it may be provided that outer seal 36 is integrally joined to base body 24 of stopper 1 and/or to housing 11, in particular to protective sleeve 15 and/or to end section 151 of protective sleeve 15 remote from the housing body, in particular fused, in particular by melting on the material which is provided for outer seal 36.

Alternatively, however, in the further exemplary embodiments it may be provided that outer seal 36 is not integrally joined to base body 24 of stopper 1 and/or to housing 11, in particular to protective sleeve 15 and/or to end section 151 of protective sleeve 15 remote from the housing body, but, rather, that outer seal 36 is merely secured, in particular in a force-fit manner, to base body 24 of stopper 1 and/or to housing 11, in particular to protective sleeve 15 and/or to end section 151 of protective sleeve 15 remote from the housing body. In this case, however, it is particularly preferred that outer seal 36 is integrally joinable, in particular weldable, to base body 24 of stopper 1 and/or to housing 11, in particular to protective sleeve 15 and/or to end section 151 of protective sleeve 15 remote from the housing body.

One exemplary embodiment of the method according to the present invention for manufacturing an exhaust gas sensor 2 provides that a base body 24 which contains polytetrafluoroethylene and has at least one axial through channel 25 is provided, that a connecting cable which on the radial exterior contains a sealing material, for example in the form of a 150-μm thick film, which contains at least one perfluoroalkoxy polymer or one tetrafluoroethylene perfluoroproylene or one polychlorotrifluoroethylene or one polyvinylidene fluoride, is led through through channel 25. In addition, it is provided that this combination of base body 24 and connecting cable 21 together with an outer seal material, for example a 150-μm thick film, which contains at least one perfluoroalkoxy polymer or one tetrafluoroethylene perfluoroproylene or one polychlorotrifluoroethylene or one polyvinylidene fluoride, is situated within a housing 11 so that the outer sealing material is situated between base body 24 and housing 11. In the present example, it is provided that the arrangement takes place in an end section 151 of a protective sleeve 15 which is remote from the housing body and is mountable together with a housing body 12 to form a housing 11.

It is provided in particular that a seal of housing 11 or of protective sleeve 15 is provided which is integrally joined, in particular overall, by caulking and heating of the combination of connecting cable 21, sealing material, base body 24, outer sealing material, and housing 11 or protective sleeve 15. In particular, fusion results from melting on the sealing material and the outer sealing material.

In the example, the caulking is carried out at an applied pressure of 700 N/cm^2 to 2000 N/cm^2. The heating of the combination of connecting cable 21, sealing material, base body 24, outer sealing material, and housing 11 is preferably carried out over a period of 10 s or longer, preferably 30 s or longer, so that melting-on of the sealing material and of the outer sealing material reliably occurs.

In the present example, it is also provided that the heating takes place up to a temperature which is above the melting temperature of the sealing material and of the outer sealing material, for example above 280° C. for a perfluoroalkoxy (PFA) polymer, above 240° C. for tetrafluoroethylene perfluoroproylene (FEP), above 190° C. for polychlorotrifluoroethylene (PCTFE), and above 170° C. for polyvinylidene fluoride (PVDF), so that melting-on of the sealing material and of the outer sealing material reliably occurs. During the heating, it is particularly important that the heating takes place in such a way that the temperature of the base body does not exceed 327° C. Chemical decomposition of the base body, and thus in particular irreversible damage to stopper 1, are reliably avoided in this way.

What is claimed is:

1. A stopper for sealing a housing of an exhaust gas sensor, comprising:
    a base body containing polytetrafluoroethylene;
    at least one through channel provided in the base body for guiding through a connecting cable; and
    a seal situated, at least in places, between the base body and the at least one through channel,
    wherein the seal contains one of perfluoroalkoxy polymer, tetrafluoroethylene perfluoroproylene, polychlorotrifluoroethylene, or polyvinylidene fluoride,
    wherein the housing is indirectly connected to the stopper via an outer seal in an integrally joined manner,
    wherein the outer seal is formed as an outer sealing ring which is radially outwardly situated on base body.

2. The stopper as recited in claim 1, wherein the base body is connected to the seal in an integrally joined manner.

3. The stopper as recited in claim 2, wherein the seal is situated on the base body in the form of a layer facing the at least one through channel and having a layer thickness of 50 μm to 250 μm.

4. An exhaust gas sensor, comprising:
    a housing;
    a stopper including:
        a base body containing polytetrafluoroethylene;
        at least one through channel provided in the base body; and
        a seal situated, at least in places, between the base body and the at least one through channel,
        wherein the seal contains one of perfluoroalkoxy polymer, tetrafluoroethylene perfluoroproylene, polychlorotrifluoroethylene, or polyvinylidene fluoride; and
    at least one connecting cable guided through the at least one through channel of the stopper,
    wherein the housing is sealed off by the stopper,
    wherein the housing is indirectly connected to the stopper via an outer seal in an integrally joined manner,
    wherein the outer seal is formed as an outer sealing ring which is radially outwardly situated on base body.

5. The exhaust gas sensor as recited in claim 4, wherein the at least one connecting cable is connected to the seal in an integrally joined manner.

6. The exhaust gas sensor as recited in claim 4, wherein the at least one connecting cable includes an electrical conductor enclosed by an insulation containing a fluoropolymer.

7. The exhaust gas sensor as recited in claim 4, wherein the at least one connecting cable, the stopper, and the housing are connected to one another, at least indirectly, in an integrally joined manner.

8. A method for manufacturing an exhaust gas sensor, comprising:
    providing a base body of a stopper, wherein the base body contains polytetrafluoroethylene, and wherein the base body has at least one through channel;
    providing a connecting cable which has on the radial exterior a sealing material containing one of perfluoroalkoxy polymer, tetrafluoroethylene perfluoroproylene, polychlorotrifluoroethylene, or polyvinylidene fluoride;
    guiding the connecting cable through the at least one through channel of the base body so that the sealing material enters into the at least one through channel;
    heating the combination of the base body, the sealing material, and the connecting cable;
    providing a housing; and
    installing the combination of the base body, the sealing material, and the connecting cable on the housing to seal off the housing,
    wherein the housing is indirectly connected to the stopper via an outer seal in an integrally joined manner,
    wherein the outer seal is formed as an outer sealing ring which is radially outwardly situated on base body.

9. The method as recited in claim 8, wherein the connecting cable radially outwardly includes the sealing material in the form of at least one of a tube, a film, and a ring.

10. The method as recited in claim 9, wherein caulking is performed in addition to the heating, the caulking being performed by an externally applied pressure of 700 N/cm$^2$ to 2000 N/cm$^2$.

11. The method as recited in claim 10, wherein the heating takes place in such a way that the sealing material at least partially melts, and an integrally joined connection is at least indirectly formed among the base body, the sealing material, and the connecting cable.

12. The method as recited in claim 11, wherein the heating takes place in such a way that the temperature of the base body does not exceed 327° C.

* * * * *